United States Patent [19]

Pechhold

[11] Patent Number: 4,958,039
[45] Date of Patent: Sep. 18, 1990

[54] MODIFIED FLUOROCARBONYLIMINO BIURETS

[75] Inventor: Engelbert Pechhold, Chadds Ford, Pa.

[73] Assignee: E. I. Du Pont de Nemours and Company, Wilmington, Del.

[21] Appl. No.: 644,089

[22] Filed: Aug. 24, 1984

[51] Int. Cl.$^5$ .................. C07F 7/10; D06M 13/28; D06M 1/00; D06M 13/40
[52] U.S. Cl. .................. 556/421; 252/8.75; 252/8.8; 564/38; 428/289; 428/290; 428/365; 428/391; 428/395; 546/292; 548/305; 548/306
[58] Field of Search .................. 564/38; 252/8.8, 8.75; 428/395, 365, 289, 391, 290; 556/427; 546/292; 548/305, 306

[56] References Cited

U.S. PATENT DOCUMENTS

| | | | |
|---|---|---|---|
| 2,145,011 | 1/1939 | Landolt et al. | 564/38 X |
| 2,309,113 | 12/1944 | Morgan et al. | 564/38 X |
| 2,764,601 | 9/1956 | Garceau | 564/38 X |
| 4,668,406 | 5/1987 | Chang | 252/8.75 |
| 4,748,267 | 5/1988 | Chang | 560/158 |

*Primary Examiner*—Paul F. Shaver

[57] ABSTRACT

Fluorocarbonylimino biurets derived from a tris-(isocyanotoalkane)biuret, a fluoroaliphatic alcohol and a modifier group imports oil/water repellency, soil-release properties.

25 Claims, No Drawings

MODIFIED FLUOROCARBONYLIMINO BIURETS

FIELD OF THE INVENTION

The present invention relates to novel modified fluorocarbonylimino biurets and their use to provide oil/water repellency, soil-release properties

PRIOR ART

U.S. Pat. No. 3,987,227 discloses carpets having a stain-repellent and soil-resistant coating formed by a combination of a water-insoluble fluoroaliphatic radical containing urethane adduct and a water insoluble urethane adduct free from fluoroaliphatic radicals.

U.S. Pat. No. 4,264,484 discloses treating carpets with a combination of:
(a) a water-insoluble addition polymer derived from polymerizable ethylenically unsaturated monomer; and
(b) a water-insoluble fluoroaliphatic radical and aliphatic chlorine-containing carboxylic or carbamic ester.

U.S. Pat. No. 4,340,749 discloses treating carpets to render them soil-resistant and stain-repellent with a carboxylic or carbamic ester of a fluoro-aliphatic radical- and aliphatic chlorine-containing alcohol.

U.S. Pat. No. 4,401,780 discloses treating textiles with a fluorochemical composition comprising a mixture of:
(a) a water-insoluble fluoroaliphatic radical and aliphatic chlorine-containing ester;
(b) a water-insoluble fluoroaliphatic radical-containing polymer; and
(c) water insoluble fluoroaliphatic radical-containing compound selected from carbonylimino compounds and imine compounds.

Br. No. 1,241,505 discloses tertiary amine salts of fluorocarbamates which are useful as oil-repellents for treating fabrics.

German Patentschrift No. 1,794,356 discloses various fluorocarbamates.

BACKGROUND AND SUMMARY OF THE INVENTION

The present invention describes novel fluorocompounds which when applied onto fibers and fabrics provide durable finishes with antisoiling properties.

Fluorocarbamates from mono- and diisocyanates have been described previously in various references, such as the references cited above, for improving oil and water resistance of textile surfaces. However, during processing such as washing and drying, a major part of these compounds is lost to the atmosphere and treatment medium, which may cause pollution and operating problems. These problems can be overcome by using reaction products of fluoroalcohols with the biurets of aliphatic or cycloaliphatic isocyanates which give rise to non-volatile and fairly durable textile finishes.

Tris(isocyanato alkane)biurets as used in the invention and their method of preparation are described in U.S. Pat. Nos. 3,124,605 and 3,201,372. It is believed that the unique biuret structure provides strong hydrogen bonding to the fiber substrate.

Further improvement in durability has been achieved by incorporation of a modifier group (R' or R" below) in the reaction product of fluoroalcohols and tris-(isocyanato alkane)biurets. A modifier group may be an aromatic, aliphatic, alicyclic compound or mixture of compounds with one or more Zerevitinov* active hydrogen atoms such as any fluorine-free monomeric alcohol or any substituted or unsubstituted fluorine-containing or fluorine-free diol, triol, tetrol, polyol, amine, diamine, triamine, tetramine, polyamine, hydroxyamine, aminothiol, thiol, dithiol, trithiol, tetrathiol, polythiol, hydroxythiol, carboxythiol, monocarboxylic acid, dicarboxylic acid, tricarboxylic acid, aminocarboxylic acid, etc.

* Zerevitinov determination is the reaction of an organic compound containing active hydrogen atoms, e.g., —OH, —COOH, —NH, etc., with methylmagnesium halide to give methane which is collected and determined volumetrically.

The novel compounds of this invention impart high oil/water repellency and good soil resistance when applied onto nylon or polyester fiber or fabric. Similar improvements may be achieved when applied to other synthetic or natural fibers or their blends.

The compounds as described in this invention can be applied onto the substrate pure or in combination with other textile or fluoro-finishes, processing aids, lubricants, anti-stains, etc., either from organic solutions or aqueous dispersions by any of the customary procedures such as spraying, dipping, padding, foaming, etc. The compounds can also be blended with other agents which have oil/water repellency and soil release properties and applied to fibers or fabrics.

DETAILED DESCRIPTION

The novel compounds of the present invention are oligomers of the formula

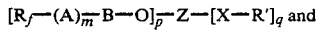 and

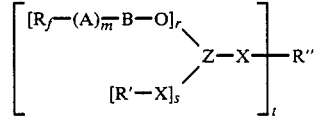

wherein
Z is a tris(carbonylimino)biuret radical of the general formula

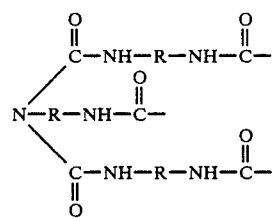

in which R is an aliphatic or cycloaliphatic residue having at least 4 and not more than 20 carbon atoms, with only alkyl, alkoxy or no substituents, especially an alkyl or cycloalkyl residue and most preferably —(CH$_2$)$_6$—.

R$_f$ is a fully-fluorinated straight or branched aliphatic radical which can be interrupted by oxygen atoms. Preferably, R$_f$ contains at least 3 and not more than 20 carbon atoms.

A is a divalent radical selected from —SO$_2$NR$_3$—, —CONR$_3$—, —S—, or —SO$_2$—, where R$_3$ is H or a C$_{1-6}$ alkyl radical.

B is a divalent linear hydrocarbon radical —C$_n$H$_{2n}$— which can be end capped by $$+OCH_2CH_2+_z, +OCH_2-\underset{\underset{CH_3}{|}}{CH}+_z, +OCH_2-\underset{\underset{CH_2Cl}{|}}{CH}+_z \text{ or}$$

$$-\underset{\underset{R_4}{|}}{\overset{\overset{R_4}{|}}{C}}+OCH_2\underset{\underset{CH_2Cl}{|}}{CH}+_z$$

where n is 0 to 12, z is 1 to 50, and $R_4$ is H or lower alkyl;

X is O, S or $NR_5$, where $R_5$ is H or a lower alkyl;

R' is any monovalent fluorine-free, substituted or unsubstituted aliphatic, alicyclic, aromatic or heterocyclic radical;

R" is any substituted or unsubstituted fluorine-containing or fluorine-free aliphatic, alicyclic, aromatic or heterocyclic radical with a valency of at least 2 and not more than 100;

m is zero or 1;
p is 1 or 2;
q is (3−p), i.e., either 2 or 1;
r is 1 or 2;
s is (2−r) i.e., either 1 or 0; and
t is an integer of 2 to 100.

Preferred in view of the ease of manufacture and their properties are the compounds of the following formula:

$$[R_f-(A)_m-B-O+_pZ-[X-R']_q$$

wherein
Z is $$N\underset{}{\overset{}{-(CH_2)_6-NH-\overset{\overset{O}{\|}}{C}-}} \begin{matrix} \overset{O}{\|} & & \overset{O}{\|} \\ C-NH-(CH_2)_6-NH-C- \\ & \overset{O}{\|} \\ & C-NH-(CH_2)_6-NH-C- \\ & \overset{O}{\|} & & \overset{O}{\|} \\ C-NH-(CH_2)_6-NH-C- \end{matrix}$$

$R_f$ is a fully-fluorinated straight or branched aliphatic radical of 3 to 20 carbon atoms which can be interrupted by oxygen atoms, more preferably, $-C_nF_{2n+1}-$ where n is 3 to 14;

A is a divalent radical selected from $-SO_2NR_3-$, $-CONR_3-$, $-S-$, or $-SO_2$, where $R_3$ is H or a $C_{1-6}$ alkyl radical, preferably A is $-SO_2NCH_3-$ or $-SO_2NC_2H_5-$;

B is a divalent linear hydrocarbon radical $-C_nH_{2n}-$ which can be end capped by $$+OCH_2CH_2+_z, +OCH_2-\underset{\underset{CH_3}{|}}{CH}+_z, +OCH_2-\underset{\underset{CH_2Cl}{|}}{CH}+_z \text{ or}$$

$$-\underset{\underset{R_4}{|}}{\overset{\overset{R_4}{|}}{C}}+OCH_2CH+_z$$
$$\phantom{-CCCCCC}|$$
$$\phantom{-CCCCCCC}CH_2Cl$$

where n is 0 to 12, z is 1 to 50, and $R_4$ is H or lower alkyl, preferably B is $-C_nH_{2n}-$ where n is 2 to 6;

X is O, S, or $NR_5$, where $R_5$ is H or lower alkyl, preferably O or NH;

R' is a monovalent fluorine-free aliphatic, alicyclic, aromatic or heterocyclic radical substituted with one or more of the following: $-Cl$, $-Br$, $-OR_6$, $-CO_2R_6$, $-Si(OR_6)_3$, $-N^{\oplus}(R_6)_3$ or vicinal $-OH/-Cl$, $-Br$, where R is alkyl of 1 to 18 carbon atoms, preferably an aliphatic radical;

m is zero or 1, preferably 0;
p is 1 or 2; and
q is (3−p), i.e., either 1 or 2.

Also preferred are compounds of the following formula:

$$\left[[R_f-B-O]_2-Z-X\right]_2-R'' \text{ wherein}$$

$$Z \text{ is } N\underset{}{\overset{}{-(CH_2)_6-NH-\overset{\overset{O}{\|}}{C}-}} \begin{matrix} \overset{O}{\|} & & \overset{O}{\|} \\ C-NH-(CH_2)_6-NH-C- \\ & \overset{O}{\|} \\ & C-NH-(CH_2)_6-NH-C- \\ & \overset{O}{\|} & & \overset{O}{\|} \\ C-NH-(CH_2)_6-NH-C- \end{matrix}$$

$R_f$ is $-C_nF_{2n+1}$, where n is 3 to 14;
B is $-C_nH_{2n}-$, where n is 2 to 6;
X is O or NH; and
R" is any substituted or unsubstituted fluorine-containing or fluorine-free aliphatic, alicyclic, aromatic or heterocyclic radical with a valency of 2.

The modified fluorocarbonylimino biurets described in this invention can be prepared by reacting a fluoroalcohol with a stoichiometric excess of a tris(isocyanato alkane)biuret at 50°–90° C. in the presence of a catalyst such as dibutyltin dilaurate. The amount of catalyst used will depend upon the charge, but is usually only a few drops, e.g., 0.02 to 0.04 parts per mole of reactants. The reaction can be carried out neat or in the presence of a dry solvent such as methyl isobutyl ketone. After 2 to 5 hours reaction is usually complete at which point the free isocyanate (NCO) is determined by the di-n-butylamine titration method. Based on this determination the appropriate amount of modifier is added, to react the residual isocyanate, usually as a solution in an organic solvent such as methyl isobutyl ketone. To allow for completion of the reaction, the mixture is heated for another 8 to 16 hours and then diluted to a 50 to 70 wt % solution with an organic solvent such as methyl isobutyl ketone.

The solution of the modified fluorocarbonylimino biurets can be dispersed in water in the usual fashion by using a surfactant which can be anionic, cationic, or nonionic or a combination of surfactants can be used.

Representative fluoroaliphatic alcohols that can be used in the reaction with tris(isocyanato alkane)biurets are:

$$C_{n'}F_{2n'+1}(CH_2)_{m'}OH$$

where n' is 3 to 14 and m' is 1 to 12;

$$(CF_3)_2CFO(CF_2CF_2)_{p'}CH_2CH_2OH$$

where p' is 1 to 5;

$$C_{n'}F_{2n'+1}CON(R_3)(CH_2)_{m'}OH$$

where $R_3$ is H or lower alkyl, n' is 3 to 14, m' is 1 to 12;

$C_{n'}F_{2n'+1}SO_2N(R_3)(CH_2)_{m'}OH$ where $R_3$, $n'$ and $m'$ are described above;

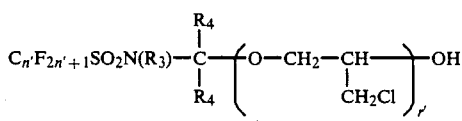

where $R_3$, $n'$, $m'$ are described above and $R_4$ is H or lower alkyl, $r'$ is 1 to 5.

Some of the representative modifiers R' or R'' that can be used to make the fluorocarbonylimino biurets of this invention are:

$C_{m''}H_{2m''+1}$—OH linear or branched $C_{m''}H_{2m''+1}$—NH$_2$ linear or branched where $m''$ is 1 to 20;

$CH_3OC_{n''}H_{2n''}$—OH where $n''$ is 2 to 20;

$H_2N$—$(CH_2)_3$—$Si(OC_2H_5)_3$;

$H_2N$—$(CH_2)_2$—NH—$(CH_2)_3$—$Si(OCH_3)_3$;

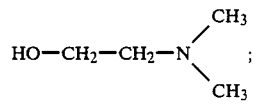

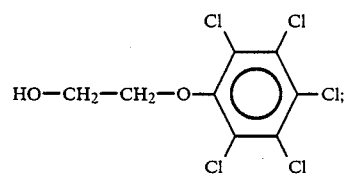

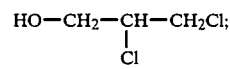

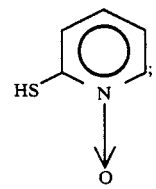

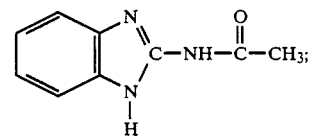

$HO$—$(CH_2)_{p''}$—$OH$;

$H_2N$—$(CH_2)_{p''}$—$NH_2$;

$H_2N$—$(CH_2)_{p''}$—$OH$ where $p''$ is 2 to 12;

$HO$—$(CH_2$—$CH_2$—$O)_{q''}$—$H$ where $q''$ is 2 to 70;

$H_2N$—$CH$—$CH_2$—$(O$—$CH_2$—$CH_2)_y$—$O$—$CH_2$—$CH$—$NH_2$
          |                                                    |
         $CH_3$                                              $CH_3$ where $y$ is 1 to 70;

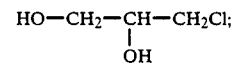

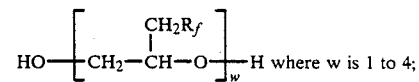 where $w$ is 1 to 4;

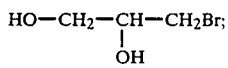

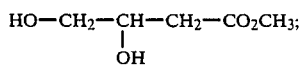

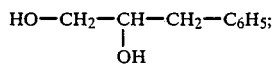

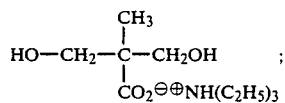

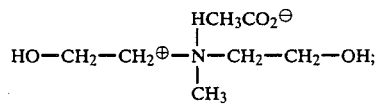

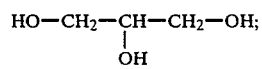

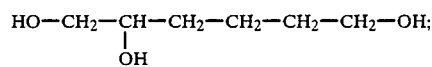

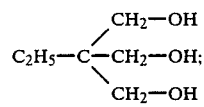

C(CH₂—OH)₄; or

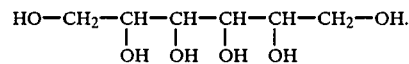

EXAMPLES

Comparative Example 1

Two moles of a mixture of fluoroalcohols of the formula F—(CF₂—CF₂)$_{n'}$—CH₂CH₂OH where n' is predominantly 5, 4, and 3, is charged to a reaction vessel and under nitrogen atmosphere heated to 50°–60° C. A 75 wt. % solution of one mole of toluene diisocyanate in methyl isobutyl ketone is added to the fluoroalcohol and the resulting reaction mixture is agitated and allowed to cool to about 45° C. at which point a catalytic amount of dibutyltin dilaurate (0.02–0.04 g) is added. An exotherm occurs. After the exotherm the reaction mixture is agitated at 85° C. for four hours at which time it is diluted to 67 wt. % solids and allowed to cool.

Comparative Example 2

Three moles of the fluoroalcohol used in the above example are charged to a reaction vessel and under a nitrogen atmosphere heated to 60°–70° C. A 75 wt. % solution of one mole of 1,3,5-tris(6-isocyanotohexyl)biuret in methyl isobutyl ketone is added to the fluoroalcohol and the resulting reaction mixture is agitated and allowed to cool to about 50° C. at which point a catalytic amount of dibutyltin dilaurate is added. An exotherm occurs. After the exotherm subsides, the reaction mixture is agitated at 85° C. for four hours at which time it is diluted to 67 wt. % solids and allowed to cool.

Example 1

Two moles of a mixture of fluoroalcohols of the formula F(CF₂CF₂)$_{n'}$CH₂CH₂OH where n' is predominantly 5, 4, and 3, is charged to a reaction vessel and under a nitrogen atmosphere heated to 60°–70° C. A 75 wt. % solution of one mole of 1,3,5-tris(6-isocyanotohexyl)biuret having the structure

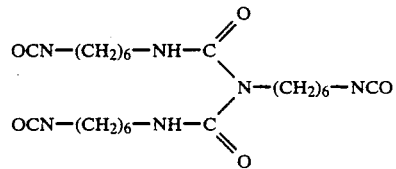

in methyl isobutyl ketone is added to the fluoroalcohol and the resulting reaction mixture is agitated and allowed to cool to about 50° C. at which point a catalytic amount of dibutyltin dilaurate is added. An exotherm occurs. After the exotherm the reaction mixture is agitated at 85° C. for three and one half hours, at which point one half mole of butanediol-1,4 is added. The reaction mixture is heated at 85° C. and agitated an additional 12 hours at which time it is diluted to 67 wt. % solids and allowed to cool.

Example 2

Two moles of the fluoroalcohol used in Example 1 are charged to a reaction vessel and under a nitrogen atmosphere heated to 60°-70° C. A 75 wt. % solution of one mole of 1,3,5-tris(6-isocyanotohexyl)biuret in methyl isobutyl ketone is added to the fluoroalcohol and the resulting reaction mixture is agitated and allowed to cool to about 50° C. at which point a catalytic amount of dibutyltin dilaurate is added. An exotherm occurs. After the exotherm subsides, the reaction mixture is agitated an additional four hours at 80° C. and one third mole of trimethylolpropane $C_2H_5C(CH_2OH)_3$ is added. The reaction mixture is heated at 85° C. and agitated for an additional 12 hours at which time it is diluted to 67 wt. % solids with methyl isobutyl ketone and allowed to cool.

Example 3

Two moles of the fluoroalcohol of Example 1 are charged to a reaction vessel and under a nitrogen atmosphere heated to 60° C.-70° C. A 75 wt. % solution of one mole of 1,3,5-tris(6-isocyanotohexyl)biuret in methyl isobutyl ketone is added to the fluoroalcohol and the reaction mixture is agitated and allowed to cool to about 50° C. at which point a catalytic amount of dibutyltin dilaurate is added. An exotherm occurs. After the exotherm subsides the reaction mixture is agitated an additional four hours at 85° C. and one half mole of the triethylamine salt of dimethylolpropionic acid

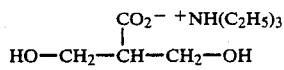

is added. The reaction mixture is heated at 85° C. an additional 12 hours at which time it is diluted to 67 wt. % solids with methyl isobutyl ketone and allowed to cool.

Example 4

Two moles of the fluoroalcohol used in Example 1 are charged to a reaction vessel and under a nitrogen atmosphere heated to 60°-70° C. A 75 wt. % solution of one mole of 1,3,5-tris(6-isocyanotohexyl)biuret in methyl isobutyl ketone is added to the fluoroalcohol and the resulting reaction mixture is agitated and allowed to cool to about 50° C. at which point a catalytic amount of dibutyltin dilaurate is added. An exotherm occurs. After the exotherm subsides the reaction mixture is agitated an additional three and one half hours at 85° C. and one half mole of N-methyl diethanolamine is added. The reaction mixture is heated at 85° C. for an additional 12 hours at which time one half mole of acetic acid is added. It is then diluted to 67 wt. % solids with methyl isobutyl ketone and allowed to cool.

Example 5

Two moles of the fluoroalcohol used in Example 1 are charged to a reaction vessel and under a nitrogen atmosphere heated to 60°-70° C. A 75 wt. % solution of one mole 1,3,5-tris(6-isocyanotohexyl)biuret in methyl isobutyl ketone is added to the fluoroalcohol and the resulting reaction mixture is agitated and allowed to cool to about 50° C. at which a catalytic amount of dibutyltin dilaurate is added. An exotherm occurs. After the exotherm subsides the reaction mixture is agitated an additional four hours at 85° C. and one half mole of polyoxyalkylene diamine such as

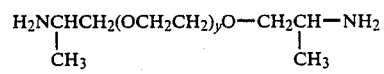

where y is 18 is added. The reaction mixture is heated at 85° C. and agitated an additional 12 hours at which time it is diluted to 67 wt. % solids and allowed to cool.

Example 6

Two and one half moles of the fluoroalcohol used in Example 1 are charged to a reaction vessel and under a nitrogen atmosphere heated to 60°-70° C. A 75 wt. % solution of one mole of 1,3,5-tris(6-isocyanotohexyl)biuret in methyl isobutyl ketone is added to the fluoroalcohol and the resulting reaction mixture is agitated and allowed to cool to about 50° C. at which point a catalytic amount of dibutyltin dilaurate is added. An exotherm occurs. After the exotherm subsides, the reaction mixture is agitated an additional four hours at 85° C. and one half mole of 3-chloro-1,2-propanediol is added. The reaction mixture is heated at 85° C. and agitated an additional 12 hours at which time it is diluted to 67 wt. % solids with methyl isobutyl ketone and allowed to cool. The product is a mixture which may have the idealized structure shown below:

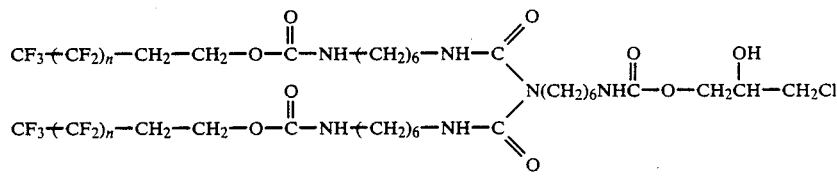

and

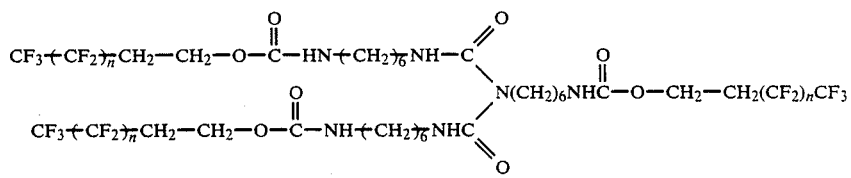

Example 7

Two moles of the fluoroalcohol used in Example 1 are charged to a reaction vessel and heated to 60°-70° C. under a nitrogen atmosphere. A 75 wt. % solution of one mole of 1,3,5-tris(6-isocyanotohexyl)biuret in methyl isobutyl ketone is added to the fluoroalcohol and the resulting mixture is agitated and allowed to cool to about 50° at which point a catalytic amount of dibutyltin dilaurate is added. An exotherm occurs. After the exotherm subsides, the reaction mixture is agitated an additional four hours at 85° C. and one mole of γ-aminopropyltriethoxysilane $H_2N(CH_2)_3Si(OC_2H_5)_3$ is added. The reaction mixture is heated at 85° C. and agitated an additional 12 hours at which time it is diluted to 67 wt. % solids with methyl isobutyl ketone and allowed to cool.

Example 8

Two moles of the fluoroalcohol used in Example 1 are charged to a reaction vessel and under a nitrogen atmosphere heated to 60°-70° C. A 75 wt. % solution of one mole of 1,3,5-tris(6-isocyanotohexyl)biuret in methyl isobutyl ketone is added to the fluoroalcohol and the resulting reaction mixture is agitated and allowed to cool to about 50° C. at which point a catalytic amount of dibutyltin dilaurate is added. An exotherm occurs. After the exotherm subsides the reaction mixture is agitated an additional four hours at 85° C. and one mole of 2-hydroxyethyl pentachlorophenoxide is added. The reaction mixture is heated at 85° C. and agitated an additional 12 hours at which time it is diluted to 67 wt. % solids with methyl isobutyl ketone and allowed to cool.

The stability and durability of the fluorocompounds of this invention are illustrated in Table I. Nylon-66 knit fabric was padded with an aqueous anionic dispersion of the fluorocompounds so as to allow a coverage of about 0.1 wt. % fluorine by weight of dry fabric. The air dried samples were tested for oil and water repellency as described below. Part of the air dried samples were annealed for two minutes in a circulating air oven at 200° C. and again tested for oil/water repellency. The above annealed samples were then subjected to five standard home washing cycles and retested.

The home washes were carried out in a "Kenmore" washing machine at 40° C., employing 28 g of "Tide" detergent per washload, followed by drying for 30 minutes in an automatic dryer at medium setting.

Oil and Water-Repellency Tests (Adapted From AATCC Test Method 118)

A piece of fabric, treated with a solution or aqueous dispersion of the polymers of this invention, is conditioned for a minimum of 2 hours at 23°±2° and 65±10% relative humidity. The repellency of carpet samples should be measured on the side of the yarn, not on the tips of the tufts. Beginning with the lowest numbered test liquid (Repellency Rating No. 1), one drop (approximately 5 mm diameter or 0.05-ml volume) is placed on each of three locations at least 5 mm apart. The drops are observed for 10 seconds for the water-repellency test, 30 seconds for the oil-repellency test. If, at the end of those periods of time, two of the three drops are still spherical to hemispherical in shape with no wicking around the drops, three drops of the next higher numbered test liquid are placed on adjacent sites and observed again for the specified periods of time. The procedure is continued until one of the test liquids results in two of the three drops failing to remain spherical or hemispherical, or wetting or wicking occurs. The oil-repellency rating and the water-repellency rating of the yarn, fabric or carpet each is the highest numbered test liquid for which two of three drops remain spherical or hemispherical with no wicking for the specified time.

| STANDARD WATER TEST LIQUIDS | | |
|---|---|---|
| | Composition (Volume %) | |
| Water-Repellency Rating Number | Isopropanol (Reagent Grade) | Distilled $H_2O$ |
| 1 | 2 | 98 |
| 2 | 5 | 95 |
| 3 | 10 | 90 |
| 4 | 20 | 80 |
| 5 | 30 | 70 |

Dry Soiling Test

Treated and untreated carpets are exposed simultaneously to floor traffic for 10,000 footsteps. They are then removed from the floor and vacuumed. Then a class rating to indicate degree of retained soil is assigned to the treated carpets using the untreated carpet as the basis for comparison.

Wet Soiling Test

A slurry of dirt and water is prepared. A shoe sole is dipped into the slurry and then pressed down in the same manner on each of the treated and untreated carpets to be tested. Following air drying and vacuuming, a class rating is assigned exactly as in Dry Soiling (above).

| | Scale of Visual Rating |
|---|---|
| Rating | Appearance Compared to Control |
| 1 W | Worse |
| 0 | Control |
| 1 | Slightly Better |
| 2 | Better |
| 3 | Much Better |
| 4 | Significantly Better |
| 5 | Best - Completely Unsoiled |

| STANDARD OIL TEST LIQUIDS | |
|---|---|
| Oil-Repellency Rating Number | Composition |
| 1 | "Nujol"* |
| 2 | 65/35 "Nujol"/n-hexadecane by volume at 21° C. |
| 3 | n-hexadecane |
| 4 | n-tetradecane |
| 5 | n-dodecane |
| 6 | n-decane |

*"Nujol" is the trademark of Plough, Inc., for a mineral oil which has a Saybolt viscosity of 360/390 at 38° and a specific gravity of 0.880/0.900 at 15° C.

TABLE I

| | Air Dried Oil/Water | 2 Min. at 200° C. Oil/Water | 2 Min at 200° C. 5 Home Washings Oil/Water |
|---|---|---|---|
| Comparative Example 1 | 2/3 | 0/3 | 0/0 |
| Comparative Example 2 | 0/2 | 6/5 | 0/4 |
| Example 1 | 0/3 | 6/5 | 6/5 |
| Example 4* | 6/5 | 6/5 | 6/5 |
| Example 6 | 0/1 | 6/5 | 6/5 |
| Example 7 | 0/2 | 6/5 | 6/5 |
| Example 8 | 0/3 | 5/5 | 5/5 |

*Self-dispersing - no surfactant

The soil release performance of several of the above exemplified fluorocompounds is tested and compared with an untreated fabric as well as three known soil repellents. The soil repellents are applied to the carpet by padding with the nip rolls set so that after drying 0.075 wt. % of carbon-bonded fluorine remain on the carpet. The carpet used is a standard yellow 30 oz./sq. yard (1.07 Kg/m²) carpet. The results are reported in Table II.

TABLE II

| Soil Repellent | Oil Repellency Test | Water Repellency Test | Dry Soil Test | Wet Soil Test |
|---|---|---|---|---|
| Ex 2 | 4 | 5 | 5 | 5 |
| Ex 3 | 2 | 4 | 4–5 | 5–4 |
| Ex 6 | 4 | 4–5 | 5 | 5 |
| Ex 7 | 3 | 5 | 4–5 | 5 |
| Commercial Compound A | 4 | 4 | 2–3 | 4 |
| Commercial Compound B | 2 | 4 | 2–3 | 5–4 |
| Commercial Compound C | 2 | 4 | 2–3 | 5 |
| Control (untreated fabric) | 0 | 1 | 0 | 0 |

In Examples 9 through 11 the active hydrogen in the modifier is underlined in the structural formula reported.

Example 9

Two moles of the fluoroalcohol used in Example 1 are charged to a reaction vessel and heated to 60°–70° C. under a nitrogen atmosphere. A 75 wt. % solution of one mole of 1,3,5-tris(6-isocyanotohexyl)biuret in methyl isobutyl ketone is added to the fluoroalcohol and the resulting mixture is agitated and allowed to cool to about 50° C. at which point a catalytic amount of dibutyltin dilaurate is added. An exotherm occurs. After the exotherm subsides, the reaction mixture is agitated an additional four hours at 85° C. and one mole of

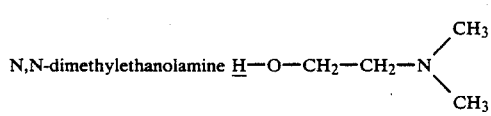

N,N-dimethylethanolamine H—O—CH₂—CH₂—N(CH₃)₂ is added. The reaction mixture is heated at 85° C. and agitated for 12 hours at which time one mole of 1-bromododecane is added and the mixture agitated for an additional 24 hours at 85°–95° C. The product is then diluted to 67 wt. % solids with methyl isobutyl ketone and allowed to cool.

Example 10

Two moles of the fluoroalcohol used in Example 1 are charged to a reaction vessel and heated to 60°–70° C. under a nitrogen atmosphere. A 75 wt. % solution of one mole of 1,3,5-tris(6-isocyanotohexyl)biuret in methyl isobutyl ketone is added to the fluoroalcohol and the resulting mixture is agitated and allowed to cool to about 50° at which point a catalytic amount of dibutyltin dilaurate is added. An exotherm occurs. After the exotherm subsides, the reaction mixture is agitated an additional four hours at 85° C. and one mole of

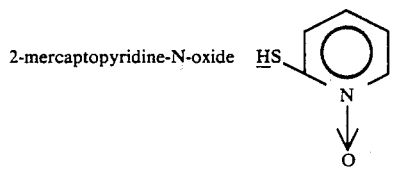

2-mercaptopyridine-N-oxide is added. The reaction mixture is heated at 85° C. and agitated an additional 12 hours at which time it is diluted to 67 wt. % solids with methyl isobutyl ketone and allowed to cool.

Example 11

Two moles of the fluoroalcohol used in Example 1 are charged to a reaction vessel and heated to 60°–70° C. under a nitrogen atmosphere. A 75 wt. % solution of one mole of 1,3,5-tris(6-isocyanotohexyl)biuret in methyl isobutyl ketone is added to the fluoroalcohol and the resulting mixture is agitated and allowed to cool to about 50° C. at which point a catalytic amount of dibutyltin dilaurate is added. An exotherm occurs. After the exotherm subsides, the reaction mixture is agitated an additional four hours at 85° C. and one mole of

methyl benzimidazole-2-carbamate
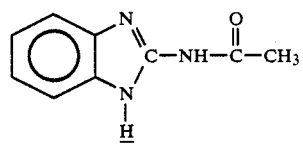

is added. The reaction mixture is heated at 85° C. and agitated an additional 12 hours at which time it is diluted to 67 wt. % solids with methyl isobutyl ketone and allowed to cool.

I claim:

1. A fluorocarbonylimino biuret of the formula:

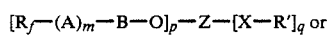

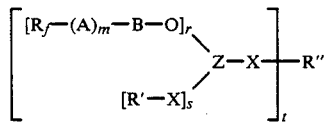

wherein

Z is a tris-(carbonylimino)biuret radical of the general formula

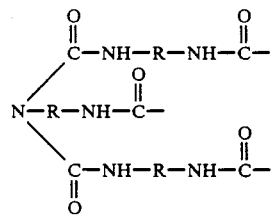

in which R is an aliphatic or cycloaliphatic residue of 4 to 20 carbon atoms, optionally substituted with alkyl or alkoxy substituents;

$R_f$ is a fully-fluorinated straight or branched aliphatic radical of 3 to 20 carbon atoms which can be interrupted by oxygen atoms;

A is a divalent radical consisting of $-SO_2NR_313$, $-CONR_3$, $-S-$, or $-SO_2-$, wherein $R_3$ is H or alkyl or 1 to 6 carbon atoms;

B is a divalent linear hydrocarbon radical $-C_nH_{2n}-$ which can be end-capped by

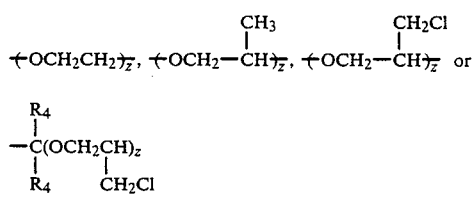

$$-\underset{\underset{R_4}{|}}{\overset{\overset{R_4}{|}}{C}}(OCH_2CH)_z$$
$$\phantom{-C(OCH_2CH)_z}CH_2Cl$$

wherein n is 0 to 12, z is 1 to 50, and $R_4$ is H or lower alkyl;

X is O, S or $NR_5$, wherein $R_5$ is H or lower alkyl;

R' is a monovalent fluorine-free alicyclic, aromatic or heterocyclic radical substituted with one or more of the following: $-Cl$, $-Br$, $OR_6$, $CO_2R_6$, $-Si(OR_6)_3$, $-N^\oplus(R_6)_3$ or vicinal $-OH/-Cl$ or $-OH/-Br$, wherein $R_6$ is alkyl 1 to 18 carbon atoms, R" is any substituted or unsubstituted fluorine containing fluorine-free aliphatic, alicyclic, aromatic or heterocyclic radical with a valency of at least 2 and not more than 100;

m is zero or 1;
p is 1 or 2;
q is (3−p), i.e., either 2 or 1;
r is 1 or 2;
s is (2−r); and
t is an integer of 2 to 100.

2. A fluorocarbonyl biuret of the formula:

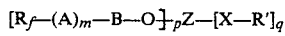

wherein
Z is

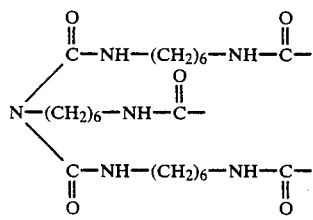

$R_f$ is a fully-fluorinated straight or branched aliphatic radical of 3 to 20 carbon atoms which can be interrupted by oxygen atoms;

A is a divalent radical selected from $-SO_2NR_3-$, $-CONR_3-$, $-S-$, or $-SO_2$, where $R_3$ is H or alkyl of 1 to 6 carbon atoms;

B is a divalent linear hydrocarbon radical $-C_nH_{2n}-$ which can be end capped by

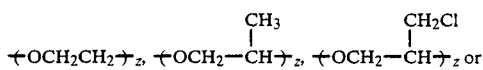

-continued

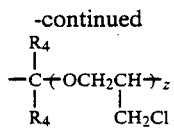

where n is 0 to 12, z is 1 to 50, and $R_4$ is H or lower alkyl;

X is O, S, or $NR_5$, where $R_5$ is H or lower alkyl;

R' is a monovalent fluorine-free aliphatic, alicyclic, aromatic or heterocyclic hydrocarbon radical substituted with one or more of the following: $-Cl$, $-Br$, $-OR_6$, $-CO_2R_6$, $-Si'(OR_6)_3$, $-N^\oplus(R_6)_3$ or vicinal $-OH/-Cl$, $-Br$, where $R_6$ is alkyl of 1 to 18 carbon atoms;

m is 0 or 1;
p is 1 or 2; and
q is (3−p).

3. A fluorocarbonylimino biuret according to claim 2 wherein
$R_f$ is $-C_nF_{2n+1}$, where n is 3 to 14;
A is $-SO_2NCH_3-$ or $-SO_2NC_2H_5-$;
B is $-C_nH_{2n}-$, where n is 2 to 6;
X is O or NH; and
R' is aliphatic.

4. A fluorocarbonylimino biuret according to claim 3 wherein m is zero; p is 2; and q is 1.

5. A fluorocarbonylimino biuret according to claim 4 wherein
R' is

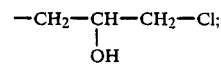

and X is oxygen.

6. A fluorocarbonylimino biuret according to claim 4 wherein
R' is

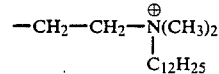

and X is oxygen.

7. A fluorocarbonylimino biuret according to claim 4 wherein
R' is $-(CH_2)_3-Si(OC_2H_5)_3$ and X is NH.

8. A fluorocarbonylimino biuret according to claim 4 wherein
R' is

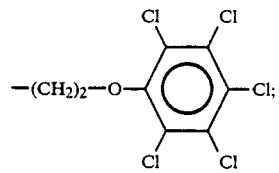

and X is oxygen.

9. A fluorocarbonylimino biuret of the formula
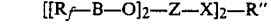

wherein
Z is

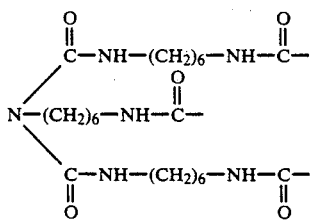

$R_f$ is $-C_nF_{2n+1}$, where n is 3 to 14;
B is $-C_nH_{2n}-$, where n is 2 to 6;
X is O or NH; and
R″ is any substituted or unsubstituted fluorine-containing or fluorine-free aliphatic, alicyclic, aromatic or hetero-cyclic radical with a valency of 2.

10. A fluorocarbonylimino biuret according to claim 9 wherein
X is oxygen and
R″ is $-(CH_2)_4-$.

11. A fluorocarbonylimino biuret according to claim 9 wherein
X is oxygen; and
R″ is

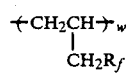

in which $R_f$ is a fluorinated aliphatic radical of at least four fully fluorinated carbon atoms and w is 1 to 4.

12. A fluorocarbonylimino biuret according to claim 9 wherein
X is oxygen and
R″ is

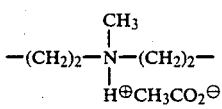

13. A fluorocarbonylimino biuret according to claim 9 wherein

R″ is

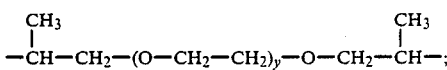

X is NH; and
y is 18.

14. A synthetic or natural fiber or fabric treated with a fluorocarbonylimino biuret according to claim 1 to impart oil/water repellency and soil resistance.

15. A synthetic or natural fiber or fabric treated with a fluorocarbonylimino biuret according to claim 2 to impart oil/water repellency and soil resistance.

16. A synthetic or natural fiber or fabric treated with a fluorocarbonylimino biuret according to claim 9 to impart oil/water repellency and soil resistance.

17. A nylon or polyester fiber or fabric treated with a fluorocarbonylimino biuret according to claim 1 to impart oil/water repellency and soil resistance.

18. A nylon or polyester fiber or fabric treated with a fluorocarbonylimino biuret according to claim 2 to impart oil/water repellency and soil resistance.

19. A nylon or polyester fiber or fabric treated with a fluorocarbonylimino biuret according to claim 9 to impart oil/water repellency and soil resistance.

20. A nylon or polyester fiber or fabric treated with a blend of a fluorochemical according to claim 1 and other textile finishing agents to impart oil/water repellency and soil resistance.

21. A fluorocarbonylimino biuret according to claim 5 comprising

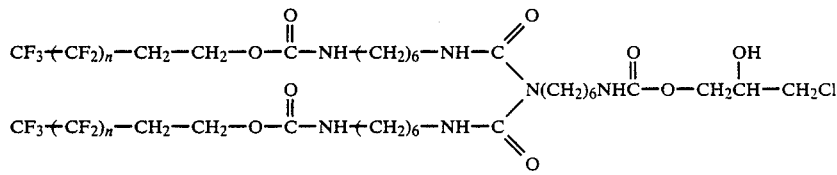

22. An antisoiling composition comprising a mixture of the compound of claim 21 and

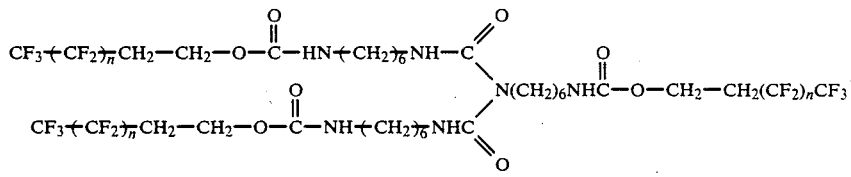

wherein n is 3, 4, 5 or mixtures thereof.

23. A synthetic or natural fiber or fabric treated with a fluorocarbonylimino biuret according to claim 21 to impart oil/water repellency and soil resistance.

24. A nylon or polyester fiber or fabric treated with a fluorocarbonylimino biuret according to claim 21 to impart oil/water repellency and soil resistance.

25. A nylon or polyester fiber or fabric treated with a blend of a fluorochemical according to claim 21 and other textile finishing agents to impart oil/water repellency and soil resistance.

* * * * *